United States Patent
Adger et al.

(10) Patent No.: US 7,232,933 B2
(45) Date of Patent: Jun. 19, 2007

(54) PREPARATION AND USE OF DIOLS

(75) Inventors: Brian Michael Adger, Cambridge (GB); Erick Moran Carreira, Zumikon (CH)

(73) Assignee: Johnson Matthey PLC, London (GB)

( * ) Notice: Subject to any disclaimer, the term of this patent is extended or adjusted under 35 U.S.C. 154(b) by 577 days.

(21) Appl. No.: 10/478,902

(22) PCT Filed: Apr. 29, 2002

(86) PCT No.: PCT/GB02/01958

§ 371 (c)(1), (2), (4) Date: Nov. 24, 2003

(87) PCT Pub. No.: WO02/094741

PCT Pub. Date: Nov. 28, 2002

(65) Prior Publication Data

US 2004/0143143 A1    Jul. 22, 2004

(30) Foreign Application Priority Data

May 23, 2001 (GB) ................................. 0112522.8

(51) Int. Cl.
- *C07C 53/00* (2006.01)
- *C07C 33/04* (2006.01)
- *C07C 31/18* (2006.01)

(52) U.S. Cl. ...................... 568/874; 568/873; 568/855; 568/715

(58) Field of Classification Search ...................... None
See application file for complete search history.

(56) References Cited

U.S. PATENT DOCUMENTS 6,586,644 B2 * 7/2003 Carreira ...................... 568/874

FOREIGN PATENT DOCUMENTS

EP    0 606 044 A1 *  7/1994

OTHER PUBLICATIONS

D. Boyall, F. López, H. Sasaki, D. Frantz, and E. M. Carreira, "Enantioselective Addition of 2-Methyl-3-butyn-2-ol to Aldehydes: Preparation of 3-Hydroxy-1-butynes," *Organic Letters*, 2000, vol. 2, No. 26, pp. 4233-4236.

Doug E. Frantz, Roger Fässler, and Erick M. Carreira, "Facile Enantioselective Synthesis of Propargylic Alcohols by Direct Addition of Terminal Alkynes to Aldehydes," *J. Am. Chem. Soc.*, 2000, vol. 122, No. 8, pp. 1806-1807.

Jordi Bach, Ramon Berenguer, Jordi Garcia, Teresa Loscertales, Judith Manzanan, and Jaume Vilarrasa, Stereoselective Reduction of Unsaturated 1,4-Diketones. A Practical Route to Chiral 1,4-Diols, *Tetrahedron Letters*, 1997, vol. 38, No. 6, pp. 1091-1094.

Kuo-Ming Wu, M. Mark Midland, and William H. Okamura, "Structural Effects on [1,5]-Sigmatropic Hydrogen Shifts of Vinylallenes," *J. Org. Chem.*, 1990, vol. 55, No. 14, pp. 4381-4392.

Mark J. Burk, T. Gregory P. Harper, and Christopher S. Kalberg, "Highly Enantioselective Hydrogenation of β-Keto Esters under Mild Conditions," *J. Am. Chem. Soc.*, 1995, Vo. 117, No. 15, pp. 4423-4424.

International Search Report dated Aug. 6, 2002, from International Application No. PCT/GB02/01958.

* cited by examiner

*Primary Examiner*—James O. Wilson
*Assistant Examiner*—Yevgeny Valenrod
(74) *Attorney, Agent, or Firm*—RatnerPrestia

(57) ABSTRACT

A process for the preparation of diols by a Lewis acid-catalysed aldehyde addition reaction on hydroxyalkynes followed by hydrogenation is described. The process provides a wide range of diols from simple, readily available starting materials. In particular the process is suitable for preparing chiral 1,4-diols suitable for the preparation of chiral phospholane ligands for use in asymmetric catalysis.

13 Claims, No Drawings

PREPARATION AND USE OF DIOLS

This is a U.S. national phase application of International Application No. PCT/GB02/01958.

This invention relates to a process for the preparation of diols. In particular it relates to the preparation of diols useful in the preparation of cyclic phosphines.

Chiral diols are of considerable interest in the fine chemicals industry where they provide a source of asymmetry useful in preparing chiral products. Chiral diols may for example be used to prepare chiral cyclic phosphines. In particular, enantiomerically pure homochiral 1,4 diols are important intermediates for the synthesis of chiral phospholanes which are $C_2$ symmetric ligands used for the construction of asymmetric catalysts. The term "chiral" refers to a structure that does not have an improper rotation axis ($S_n$), i.e., it belongs to point group $C_n$ or $D_n$. Such molecules are thus chiral with respect to an axis, plane or centre of asymmetry. The term "homochiral" refers to a structure having two, or more, chiral centres having the same conformation. A well known example of a chiral phospholane is DUPHOS. Catalysts prepared using DUPHOS and other such phosphines are used for example, for asymmetric hydrogenation to afford a wide range of industrially important compounds, generally with high optical purity and in high yield. Due to the complexity of ligand synthesis, only methyl and ethyl DUPHOS-phospholane ligands have been extensively studied. Furthermore, the current synthesis is inefficient as it requires the use of racemic diols such as hexane-2,5-diol. A difficult and lengthy process is required to separate the mixture of racemate and meso-forms into the required homochiral forms and provides at best, a yield of each enantiomer of 25%. Finally, because of the limited routes available, the range of homochiral diols achieved by the existing methods is currently narrow, providing limited scope for development of new catalysts.

The synthetic preparation of chiral alcohols is known. In particular, the preparation of chiral propargyl alcohols, such as 3-hydroxy-1-butyne, using zinc triflate in an enantioselective aldehyde addition reaction to an alkyne, in the presence of triethylamine and (+)- or (−)-N-methylephedrine in known. (See for example, Carreira et al, *Organic Letters*, 2000, 2(26), 4233-4236). This reaction has been used to provide chiral propargyl alcohols, via, for example, thermally unstable alkyne diols. We have discovered that useful diols may be prepared by reacting an aldehyde with a hydroxyalkyne and hydrogenating the resulting dihydroxyalkyne product.

Accordingly this invention provides a process for the preparation of a diol comprising the steps of;
(a) Performing an addition reaction between an aldehyde and a hydroxyalkyne in the presence of a Lewis acid and optionally in the presence of a chiral ligand capable of reaction with said Lewis acid, to produce a dihydroxyalkyne and
(b) Hydrogenating the dihydroxyalkyne.

The aldehyde is of general formula $R^1C(O)H$ in which $R^1$ represents a saturated or unsaturated alkyl (having between 2 and 24 carbon atoms), cycloalkyl or aryl group which may be substituted or unsubstituted. Substituting groups may be alkyl, aryl, halogen, hydroxyl or siloxy groups. For example $R^1$ may be ethyl, n-propyl, iso-propyl, n-butyl, iso-butyl, tert-butyl, n-amyl, iso-amyl, tert-amyl, n-hexyl, cyclo-hexyl, phenyl, di-tertbutylphenyl, phenyl, PhCH=CH and iso-$Pr_3SiO(CH_2)_2$. Preferred aldehydes are cyclohexanecarboxaldehyde, benzaldehyde, iso-butyraldehyde, butyraldehyde, iso-valeraldehyde, 2-methylbutyraldehyde, trimethylacetaldehyde, valeraldehyde and propaldehyde.

The hydroxyalkyne is of general formula $R^2R^3C(OH)(CH_2)_xC\equiv CH$ in which $C\equiv C$ represents a carbon-carbon triple bond. $R^2$ represents a saturated or unsaturated alkyl (having between 2 and 24 carbon atoms), cycloalkyl or aryl group which may be substituted or unsubstituted. Substituting groups may be alkyl, aryl, halogen, hydroxyl or siloxy groups. For example $R^2$ may be ethyl, n-propyl, iso-propyl, n-butyl, iso-butyl, tert-butyl, n-amyl, iso-amyl, tert-amyl, n-hexyl, cyclo-hexyl, phenyl, di-tertbutylphenyl, PhCH=CH and iso-$Pr_3SiO(CH_2)_2$. $R^3$ represents H or a saturated or unsaturated alkyl (having between 2 and 24 carbon atoms), cycloalkyl or aryl group which may be substituted or unsubstituted. Substituting groups may be alkyl, aryl, halogen, hydroxyl or siloxy groups. $R^2$ and $R^3$ may be the same but are preferably different to provide a chiral hydroxyalkyne in which the hydroxyl group is bound to a chiral centre. Most preferably $R^3$ is H. The hydroxyalkyne is therefore preferably a chiral hydroxyalkyne. x may be 0 to 12 but is preferably 0, 1, or 2 to yield a 1,4-, 1,5- or 1,6-dihydroxyalkyne. Most preferably x is 0 and the product is a 1,4-dihydroxyalkyne.

The dihydroxyalkyne product is of formula $R^2R^3C(OH)(CH_2)_xC\equiv CCH(OH)R^1$ in which $R^1$ and $R^2$ may be the same or different. Hence, where x is 0 and $R^3$ is hydrogen the dihydroxyalkyne product has the formula $R^2CH(OH)C\equiv CCH(OH)R^1$, $R^1$ and $R^2$ are preferably the same to provide a diol having the potential to provide a cyclic phosphine having $C_2$ symmetry.

The hydroxyalkyne may itself be prepared by an aldehyde addition reaction to an alkyne. In particular, a chiral hydroxyalkyne may be prepared by an aldehyde addition reaction to an alkyne in the presence of a Lewis acid, a chiral ligand and a base, according to the method of Carreira et al, *Organic Letters*, 2000, 2(26), 4233-4236. The aldehyde used for preparing the chiral hydroxyalkyne is preferably of formula $R^1C(O)H$ as hereinbefore defined. The alkyne used for preparing the chiral hydroxyalkyne may be any alkyne having a terminal hydrogen, ie a C≡C-H group, for example a saturated solution of acetylene in a pressurised, sealed vessel may be used. However, it is reported by Carreira et al that a particularly useful group of alkynes are those that undergo thermal fragmentation reactions. These alkynes are readily available and relatively easy to handle compared to acetylene. In one example, the alkyne is of general formula $R^4R^5C(OH)C\equiv CH$ in which $R^4$ and $R^5$ are the same and are selected from the group comprising methyl, ethyl and propyl. Preferably $R^4$ and $R^5$ are methyl and a preferred alkyne is 2-methyl-3-butyn-2-ol. The reaction product is subjected to a thermal fragmentation reaction to yield a chiral hydroxyalkyne suitable for reaction with an aldehyde according to the process of the present invention. In a second example, the alkyne is an alkyne-silane, for example (triethylsilyl)acetylene. The resulting chiral hydroxyalkyne-silane is also subjected to a thermal fragmentation reaction to yield a chiral hydroxyalkyne suitable for reaction with an aldehyde according to the process of the present invention.

The reaction of aldehyde and hydroxyalkyne according to the first stage of the process of the present invention may if desired be used to produce a dihydroxyalkyne having one chiral centre to which a hydroxyl group is bound. However, if the hydroxyalkyne starting material has its hydroxyl group bound to a chiral centre, for example, a chiral hydroxyalkyne prepared according to the method of Carreria et al, then the resulting dihydroxyalkyne may be prepared with two chiral centres having one hydroxyl group bound to each. It is preferred in order to produce chiral phosphines having C2 symmetry that the dihydroxyalkyne produced in step (a) has two chiral centres with one hydroxyl group bound to each.

Step (a) of the process of the present invention is carried out in the presence of a Lewis acid and optionally a chiral ligand capable of reaction with said Lewis acid. The Lewis acid functions to catalyse the aldehyde addition reaction. The Lewis acid may be any having sufficient activity to catalyse the reaction. Preferably the Lewis acid is a strong Lewis acid, for example a metal triflate (i.e. a metal trifluoromethanesulphonate) and more preferably, the Lewis acid is selected from the group comprising copper triflate, cadmium triflate and zinc triflate. The Lewis acid may if desired be supported on an insoluble support material, for example a polymeric support or an inorganic support such as silica, a metal oxide, zeolite or an aluminosilcate to facilitate catalyst recovery and re-use.

A chiral ligand is optionally present during the first step of the present invention. In a preferred embodiment, a chiral ligand is present to effect the enantioselectivity of the reaction and hence the chirality of the resulting chiral centre. Preferably either a (+) or (−) chiral ligand is used that interacts with the Lewis acid to produce the desired effect. The terms "(+)" or "(−)" here refer to the effect of the molecular structure on the direction of rotation of plane polarized light. Hence, for example a single enantiomer (+)-ligand may provide a reaction product with a greater number of (R)-chiral centres and a (−)-ligand likewise may provide a product with a greater number of (S)-chiral centres. The chiral ligand may be any that interacts with the Lewis acid and provides sufficiently high optical purity in the reaction product. The chiral ligand is preferably a chiral β-alkanolamine, chiral β-diamine or chiral β-thioamine and most preferably is (+)- or (−)-N-alkyl- or aryl-ephedrine. A particularly suitable chiral ligand is (+)- or (−)-N-methylephedrine. In the process of the present invention (+)-N-methylephedrine produces predominantly (R)-chiral centres whilst (−)-N-methylephedrine produces predominantly (S)-chiral centres.

The product of the first step of the present invention is a dihydroxyalkyne and as stated above, preferably the product is a chiral dihydroxyalkyne having two chiral centres. Depending on whether the (+) or (−) chiral ligand was used and whether the hydroxyalkyne starting material was itself chiral and possessed predominantly an (R)- or (S)-chiral centre (opposed to a racemic mixture), the product dihydroxyalkyne may be homochiral, i.e., (R,R) or (S,S) or have one (R) and one (S) centre. If the hydroxyalkyne starting material was itself prepared by an aldehyde addition reaction to an alkyne according to the method of Carreira et al, this reaction may be used to provide the (R)- or (S)-chiral centre in the hydroxyalkyne starting material.

A base is preferably present during the first step of the process of the present invention to shorten the reaction times. The base may be an inorganic base or an organic base. Preferably the base is an organic base and more preferably the organic base is an amine. Most preferably the amine is a tertiary amine for example trimethylamine, triethylamine, triethylenediamine, or pyridine.

Furthermore, it is preferable to protect at least one hydroxyl group in the hydroxyalkyne or dihydroxyalkyne from side reactions during any or all of the steps of the process of the present invention.

Side reactions can reduce the purity and yield of the desired product and are unwanted. The protection of the hydroxyl groups may be achieved using an extensive range of protecting groups known to those skilled in the art. For example, protection may be provided by reaction of a hydroxyl group to form a carboxylic- or sulphonic acid ester. If the protecting group is a carboxylic acid ester group, a carboxylic acid, carboxylic anhydride or carboxylic acid chloride may be reacted with the hydroxyl group using, for example, a base catalyst under mild conditions in a suitable solvent. For example, a benzoate protecting group may be provided by reaction of benzoyl chloride or a substituted benzoyl chloride in the presence of triethylamine for 1-24 hours at 0° C. Alternatively, sulphonic acid esters may be prepared similarly using, for example, tosyl chloride. The resulting benzoate or tosylate esters may be hydrolysed to re-generate the hydroxyl group when desired using methods well known to those skilled in the art. For example, if the protecting group is a benzoate group, it may be removed by hydrolysis with potassium hydroxide at 15-25° C. over a period of 6 to 10 hours.

Solvents are preferably used in all steps of the process to solubilize the reactants and products and provide a heat sink for any exotherm generated during the reactions. Preferably the solvent is a hydrocarbon, an aromatic hydrocarbon, an ether, an alcohol or a chlorinated hydrocarbon. Examples of suitable solvents include dichloromethane, diethylether, tetrahydrofuran, ethanol, heptanes, toluene and xylene.

The first step of the process of the present invention is generally performed under mild conditions. For example, the reaction may be performed at temperatures ranging from 0-80° C. over a period of 0.5 to 24 hours. Preferably the reaction is performed at 15-60° C. over a period of 2 to 10 hours. The amount and stoichiometry of the Lewis acid and chiral ligand can be varied substantially, leading to an increase in the yields and enantioselectivities for a number of products. Typically in the first step of the process, the aldehyde and hydroxyalkyne are added in the range 1.3:1 to 1:1.3 moles (aldehyde: hydroxyalkyne). The Lewis acid is added at a molar ratio in the range 0.05:1 to 3:1 (Lewis acid: hydroxyalkyne). Preferably, the Lewis acid is added at sub-stoichiometric amounts in the range 0.05-0.5:1 and most preferably in the range 0.1-0.3:1. The chiral ligand may be added at a molar ratio to substantially match that of the Lewis acid if desired and if a base is added, it is used at a molar ratio in the range of 0.3:1 to 1.5:1 (base: hydroxyalkyne).

The second step of the process of the present invention is the hydrogenation of the dihydroxyalkyne. The product diol may be a saturated diol, or where hydrogenation is only partial, an alkenediol, or mixtures thereof. Selective hydrogenation of the alkyne to a saturated or unsaturated product may be achieved by selecting an appropriate catalyst, as is known in the art. For example, preparation of a saturated diol may be achieved by stirring the dihydroxyalkyne in an ethanol suspension of 10% Pd on carbon for 10-20 hours at 15-25° C. under 1 atmosphere of hydrogen. Alkenediols may be prepared, for example, using Lindlar's catalyst. Following hydrogenation, the products of the process may be separated from the Pd on carbon by filtration and the solvent removed under vacuum. If desired, the crude product may be purified by column chromatography using methods well known to those skilled in the art.

Thus, according to a further aspect of the invention we provide a diol prepared according to a process comprising the steps of;

(a) Performing an addition reaction between an aldehyde and a hydroxyalkyne in the presence of a Lewis acid and optionally a chiral ligand capable of reaction with said Lewis acid, to produce a dihydroxyalkyne and
(b) Hydrogenating the dihydroxyalkyne.

The diol of the invention is preferably a 1,4-, 1,5,- or 1,6-diol. Most preferably the diol is a chiral 1,4-, 1,5,- or 1,6-diol having two chiral centres. Chiral 1,4 diols of the invention include but are not limited to;

(1S,4S), (1R,4R), (1R,4S) and (1S,4R)-1,4-dicyclohexyl-1,4-butanediol, (1S,4S), (1R,4R), (1R,4S) and (1S,4R)-1,4-diisopropyl-1,4-butanediol, (1S,4S), (1R,4R), (1R,4S) and (1S,4R)-1,4-ditertiarybutyl-1,4-butanediol, (1S,4S), (1R,4R), (1R,4S) and (1S,4R)-1,4-diphenyl-1,4-butanediol, (1S,4S), (1R,4R), (1R,4S) and (1S,4R)-1-Cyclohexyl-4-isopropyl-1,4-butanediol, (1S,4S), (1R,4R), (1R,4S) and (1S,4R)-1-Cyclohexyl-4-tertiarybutyl-1,4-butanediol, (1S,4S), (1R,4R), (1R,4S) and (1S,4R)-1-Cyclohexyl-4-phenyl-1,4-butanediol, (1S,4S), (1R,4R), (1R,4S) and (1S,4R)-1-isopropyl-4-tertiarybutyl-1,4-butanediol, (1S,4S), (1R,4R), (1R,4S) and (1S,4R)-1-isopropyl-4-phenyl-1,4-butanediol, (1S,4S), (1R,4R), (1R,4S) and (1S,4R)-1-tertiarybutyl-4-phenyl-1,4-butanediol, (1S,4S), (1R,4R), (1R,4S) and (1S,4R)-1,4-dicyclohexyl-1,4-but-2,3-enediol, and (1S,4S), (1R,4R), (1R,4S) and (1S,4R)-1-Cyclohexyl-4-isopropyl-1,4-but-2,3-enediol.

The process of the present invention provides a wide range of diols from simple, readily available starting materials. The diols may be used, for example, in the synthesis of a range of cyclic phosphines. If chiral diols are chosen, the resulting chiral cyclic phosphines may be used for the construction of asymmetric catalysts useful for example, for asymmetric hydrogenation.

Hence, according to a further aspect of the invention we also provide a cyclic phosphine prepared according to a process comprising the steps of;
(a) Performing an addition reaction between an aldehyde and a hydroxyalkyne in the presence of a Lewis acid and optionally a chiral ligand capable of reaction with said Lewis acid, to produce a dihydroxyalkyne and
(b) Hydrogenating the dihydroxyalkyne to produce a dihydroxyalkene, and/or a dihydroxyalkane, and
(c) Reacting the dihydroxyalkene and/or dihydroxyalkane with a phosphine species.

By the term "cyclic phosphine" we mean any phosphine having a ring structure incorporating a phosphorus atom. Preferably, the cyclic phosphines have 5, 6 or 7-membered rings and most preferably the cyclic phosphines are phospholanes having a 5-membered ring incorporating a phosphorus atom. The cyclic phosphines may be prepared using a saturated diol (dihydroxyalkane) or an unsaturated diol (dihydroxyalkene) of the invention using methods well known to those skilled in the art. For example, a diol of the present invention may be activated to give a cyclic sulphate or tosylate and reacted with a phosphine species prepared from a phosphine of general formula $R^6PH_2$ in which $R^6$ is a substituted or unsubstituted alkyl (having between 1 and 24 carbon atoms), aryl, substituted aryl, ferrocenyl or ruthenocyl substituent, which may optionally support other phosphine moieties.

Cyclic phosphines of the present invention include but are not restricted to the following wherein $R^1$ and $R^2$ are hereinbefore defined;

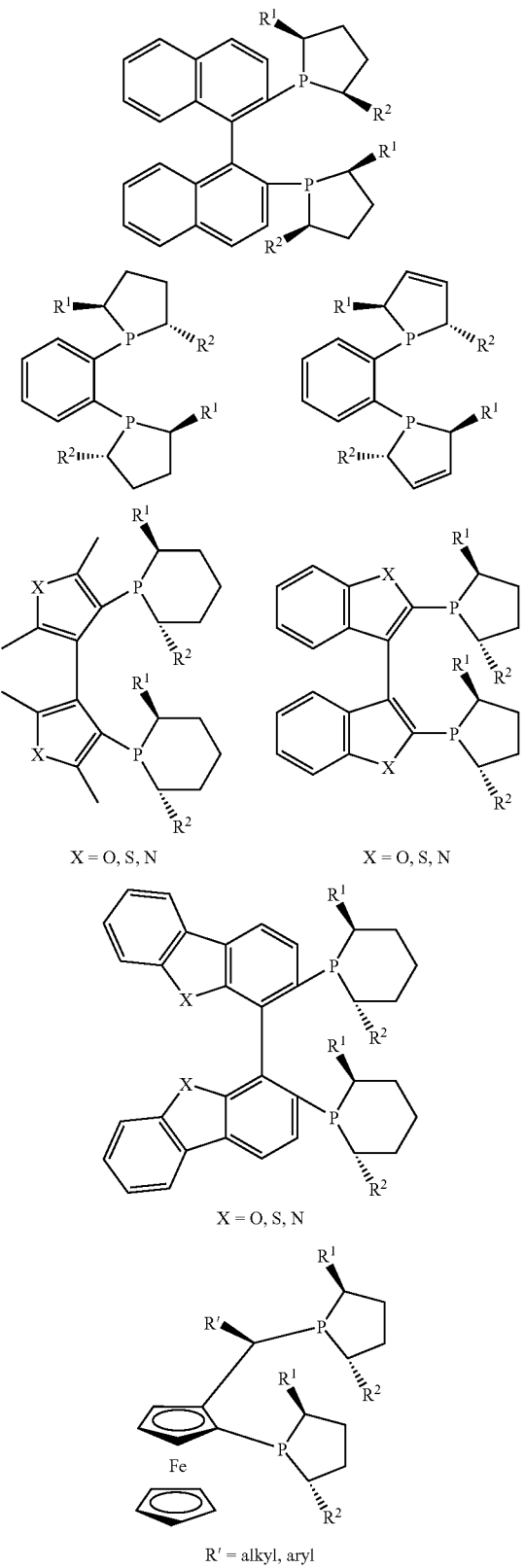

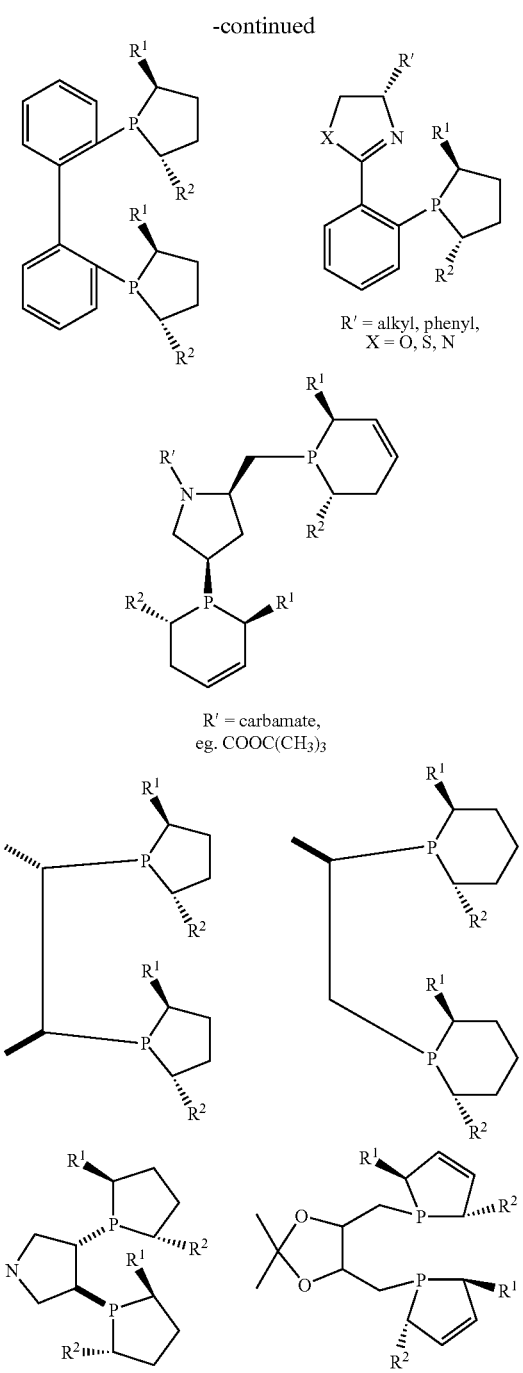

The invention is further illustrated by reference to the following examples. All reactions were performed using oven-dried glassware under an atmosphere of dry nitrogen. Toluene was distilled and dried before use. Reagents were purchased from Fluka or Aldrich chemical companies, and used without further purification except aldehydes which were distilled before use. Chiral hydroxyalkyne- and benzoate-protected chiral hydroxy alkyne-starting materials were prepared according to methods described in Carreira et al, *Organic Letters*, 2000, 2(26), 4233-4236. Chromatographic purification of products was accomplished using forced flow chromatography on silica gel 60. NMR spectra were recorded on a Varian Mercury 300 operating at 300 MHz for $^1$H NMR, and referenced to the internal solvent signals. Optical rotations were measured on a JASCO DID-1000 digital polarimeter. Thin layer chromatography was performed using silica gel 60 F254 TLC plates and visualized either with ultraviolet light or stain with CAM-Stain. HPLC analyses were carried out on a Merck Hitachi D-7000 system. Elemental compositions were determined using combustion analysis performed by the Mikroelementaranalytisches Laboratorium at the ETH, Zürich.

Examples 1 to 3 describe the preparation of 1,4 dihydroxyalkynes according to the first step of the process of the present invention. Example 1 describes the preparation of symmetrical dicyclohexyl 1,4 dihydroxyalkynes; example 2 describes the preparation of symmetrical diisopropyl 1,4 dihydroxyalkynes and example 3 describes the preparation of asymmetric 1,4 dihydroxyalkynes.

EXAMPLE 1

Synthesis of Chiral 1,4 Dihydroxyalkynes (a) Symmetrical Protected Cyclohexyl 1,4 Dihydroxyalkynes General Procedure. A 50 mL Schlenk was charged with zinc trifluoromethanesulphonate [Zn(OTf)$_2$] (400 mg, 1.1 mmol, 1.1 eq) and heated with the gun under vacuum for 5 min. (+)- or (−)-N-methylephedrine (216 mg, 1.2 mmol, 1.2 eq) was added and the flask was purged with nitrogen for 15 min. Toluene (3 mL) and triethylamine (0.17 mL, 1.2 mmol, 1.2 eq) were added. The resulting mixture was vigorously stirred at 23° C. for 2 h before the corresponding (benzoate-protected) chiral hydroxyalkyne ((R)- or (S)-Benzoic acid 1-cyclohexylpropynyl ester) (1 eq) was added. After 15 min of stirring the aldehyde (cyclohexanecarboxaldehyde) (1.1 eq) was added in one portion by syringe. The reaction was stirred and heated at 60° C. for 5 h. The mixture was quenched with NH$_4$Cl (aq) and extracted with Et$_2$O or AcOEt (3×20 mL). The combined organic layers were dried over anhydrous MgSO$_4$ and concentrated in vacuo. The residue was purified by column chromatography on silica gel using pentane:Et$_2$O (5:1 to 3:1). The (+)-ligand with the (R)-hydroxyalkyne yielded the (R,R)-product; the (−)-ligand with the (S)-hydroxyalkyne yielded the (S,S)-product and in this case the (+)-ligand with the (S)-hydroxyalkyne was used to prepare the (S,R)-product. Using this method the following dihydroxyalkynes were prepared.

(1R,4R)-Benzoic acid 4-hydroxy-1,4-dicyclohexyl-2-butynyl ester: Isolated in 75% yield and 99% ee and 90% de as determined by HPLC analysis (Chiracel OD, hexane:$^i$PrOH (99:1), 254 nm), t$_r$ 22.9 (major), 28.9 (minor), 30.4 (minor); colourless oil. $^1$H NMR (300 MHz, CDCl$_3$) δ 8.1-8.0 (m, 2H), 7.6-7.4 (m, 3H), 5.5 (dd, J=5.9 and 1.5 Hz, 1H), 4.2 (dd, J=5.9 and 1.5 Hz, 1H), 2.0-1.5 (m, 13H), 1.4-1.05 (m, 10H). Anal. Calcd. for C$_{23}$H$_{30}$O$_3$: C, 77.93%; H, 8.53%. found: C, 77.68%; H, 8.56%.

(1S,4S)-Benzoic acid 4-hydroxy-1,4-dicyclohexyl-2-butynyl ester: Isolated in 73% yield and 99% ee and 90% de as determined by HPLC analysis (Chiracel OD, hexane:$^i$PrOH (99:1), 254 nm), t$_r$ 25.2 (major), 28.9 (minor), 30.3 (minor). The spectroscopic data is the same as that in its (R,R)s enantiomer. Anal. Calcd. for C$_{23}$H$_{30}$O$_3$: C, 77.93%; H, 8.53%. found: C, 77.67%; H, 8.51%.

(1S,4R)-Benzoic acid 4-hydroxy-1,4-dicyclohexyl-2-butynyl ester: Isolated in 62% yield and 99% ee and 74% de as determined by HPLC analysis (Chiracel OD, hexane:$^i$PrOH (99:1), 254 nm), t$_r$ 23.1 (minor), 25.6 (minor), 29.4

(major); colourless oil. $[\alpha]_D^{27}$ −7.3° (c=0.28, CHCl$_3$). $^1$H NMR (300 MHz, CDCl$_3$) δ 8.1-8.0 (m, 2H), 7.6-7.4 (m, 3H), 5.5 (dd, J=5.6 and 1.35 Hz, 1H), 4.2 (m, 1H), 2.1 (d, J=5.3 Hz), 2.0-1.5 (m, 12H), 1.4-1.05 (m, 10H).

(b) Deprotection of Protected Cyclohexyl 1,4 Dihydroxyalkynes

The resulting protected dihydroxyalkynes were deprotected as follows. To a solution of the corresponding benzoate (1 eq) in Et$_2$O was added finely powdered KOH (1.5 eq) and the mixture was stirred at room temperature (23° C.) overnight (16 h). The mixture was quenched with NH$_4$Cl (aq) and extracted with Et$_2$O or AcOEt (3×20 mL). The combined organic layers were dried over anhydrous MgSO$_4$ and concentrated in vacuo. The residue was purified by column chromatography on silica gel using pentane:Et$_2$O (3:1 to 1:1): The desired chiral dihydroxyalkynes were obtained.

(S,S)-1,4-Dicyclohexyl-2-butyn-1,4-diol: Isolated in 85% yield as a white solid, m.p.=126-128° C. $^1$H NMR (300 MHz, CD$_3$OD) δ 4.9 (s, 2H), 4.1 (d, J=5.9 Hz, 2H), 1.95-1.6 (m, 10H), 1.55-1.45 (m, 2H), 1.35-1.0 (m, 10H). Anal. Calcd. for C$_{16}$H$_{26}$O$_2$: C, 76.75%; H, 10.47%; found: C, 76.55%; H, 10.43%.

(R,R)-1,4-Dicyclohexyl-2-butyn-1,4-diol: Isolated in 83% yield. The spectroscopic data are the same as its (S,S) enantiomer.

The reactions described in example 1 are depicted in reaction scheme 1.

Example 2

Synthesis of Chiral 1,4 Dihydroxyalkynes (a) Symmetrical Protected iso-propyl 1,4 Dihydroxyalkynes Following the method of example 1 the (R)-Benzoic acid 1-isopropylpropynyl ester was reacted with isobutyraldehyde to yield the desired symmetrical protected isopropyl dihydroxyalkynes.

(1R,4R)-Benzoic acid 4-hydroxy-1-isopropyl-5-methyl-2-hexynyl ester: Isolated in 76% yield (33% of pure material) and 99% ee and 86% de as determined by HPLC analysis (Chiracel OD, hexane: $^i$PrOH (99:1), 254 nm), t$_r$ 17.6 (major), 22.6 (minor); colourless oil. $^1$H NMR (300 MHz, CDCl$_3$) δ 8.1-8.0 (m, 2H), 7.6-7.4 (m, 3H), 5.5 (dd, J=5.6 and 1.6 Hz, 1H), 4.25-4.2 (m, 1H), 2.2 (d, J=5.3 Hz, 1H), 2.2-2.1 (m, 1H), 1.95-1.8 (m, 1H), 1.1 (dd, J=8.1 and 6.8 Hz, 6H), 1.0 (dd, J=6.6 and 5.9 Hz, 6H). Anal. Calcd. for C$_{17}$H$_{22}$O$_3$: C, 74.42%; H, 8.08%; found: C, 74.59%; H, 7.97%.

(1R,4S)-Benzoic acid 4-hydroxy-1-isopropyl-5-methyl-2-hexynyl ester: Isolated in 73% yield (38% of pure material) and 99% ee and 84% de as determined by HPLC analysis (Chiracel OD, hexane:$^i$PrOH (99:1), 254 nm), t$_r$ 7.9 (minor), 22.4 (major); colourless oil. $^1$H NMR (300 MHz, CDCl$_3$) δ 8.1-8.0 (m, 2H), 7.6-7.4 (m, 3H), 5.5 (dd, J=5.6 and 1.6 Hz, 1H), 4.25-4.2 (m, 1H), 2.2 (d, J=5.3 Hz, 1H),

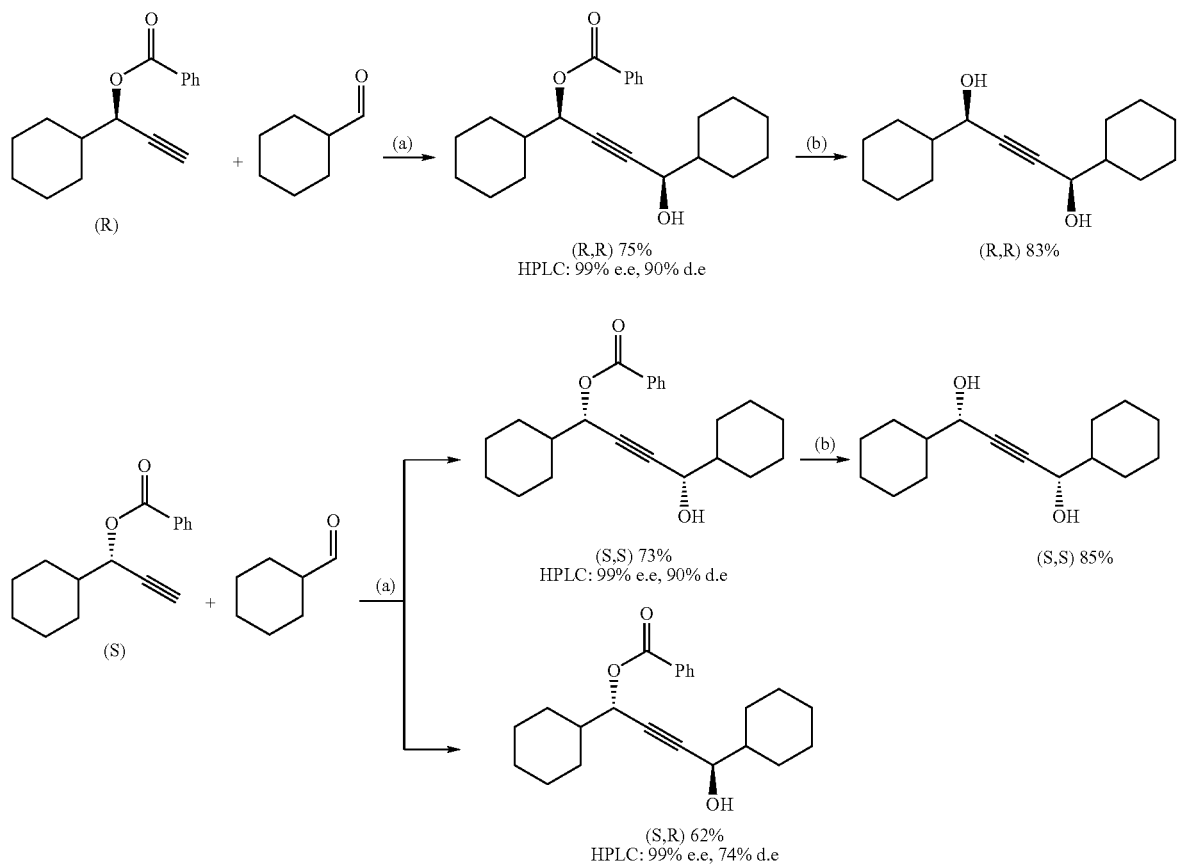

Scheme 1

2.2-2.1 (m, 1H), 1.95-1.8 (m, 1H), (dd, J=9.0 and 6.8 Hz, 6H), 1.0 (dd, J=6.5 and 6.2 Hz, 6H).

The reaction in example 2 is depicted in reaction scheme 2.

76.79%; H, 8.59%; found: C, 76.85%; H, 8.58%. The reactions described in example 3 are depicted in reaction scheme 3.

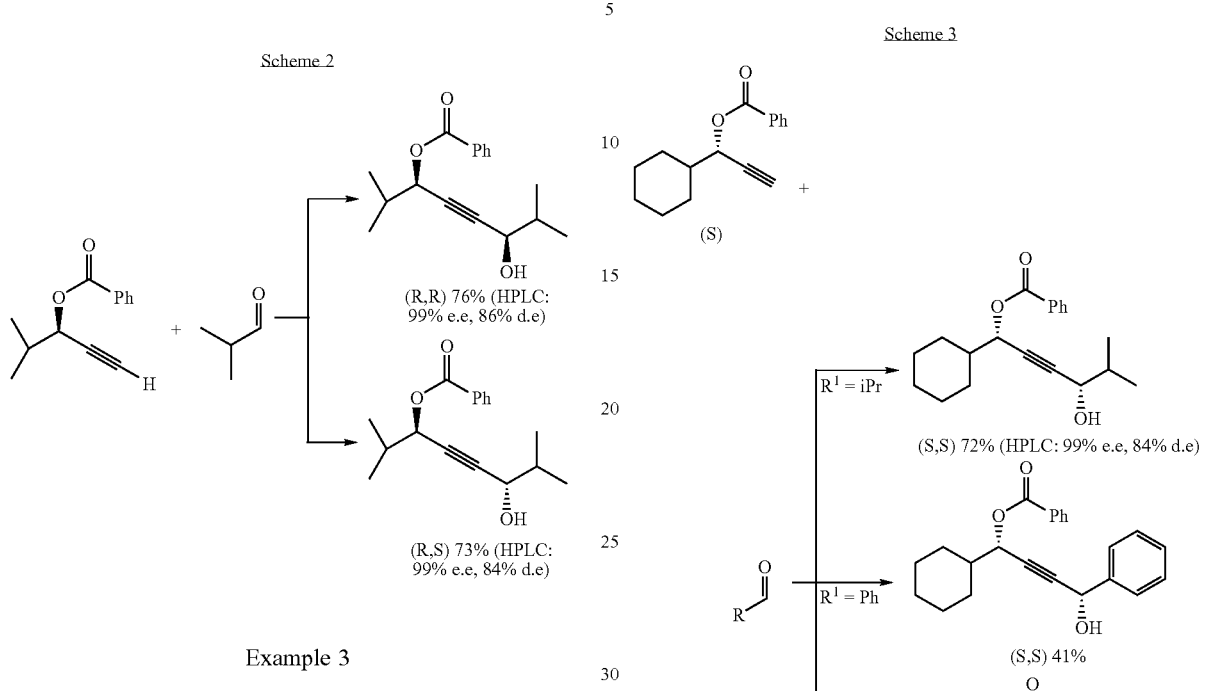

Example 3

Synthesis of Chiral 1,4 Dihydroxyalkynes (a) Unsymmetrical Protected 1,4 Dihydroxyalkynes In addition to symmetrical hydroxyalkynes, the process of the present invention is capable of providing protected non-symmetric hydroxyalkynes. In a method according to example 1, the protected (S)-cyclohyexyl alkyne, (S)-Benzoic acid 1-cyclohexylpropynyl ester, was reacted with different aldehydes where $R^1$ was iso-propyl, phenyl or tertiary-butyl. The desired non-symmetric protected hydroxyalkynes were obtained.

(1S,4S)-Benzoic acid 1-cyclohexyl-4-hydroxy-4-isopropyl-2-butynyl ester: Isolated in 72% yield and 99% ee and 84% de as determined by HPLC analysis (Chiracel OD, hexane:$^i$PrOH (99:1), 254 nm), $t_r$ 19.9 (major), 22.1 (minor); colourless oil. $^1$H NMR (300 MHz, CDCl$_3$) δ 8.1-8.0 (m, 2H), 7.6-7.4 (m, 3H), 5.5 (dd, J=5.6 and 1.6 Hz, 1H), 4.2 (dd, J=5.6 and 1.6 Hz, 1H), 2.2 (s broad, 1H, OH), 2.0-1.6 (m, 13H), 1.3-1.1 (m, 10H), 1.0-0.95 (m, 6H). Anal. Calcd. for $C_{20}H_{26}O_3$: C, 76.40%; H, 8.33%; found: C, 76.57%; H, 8.43%.

(1S,4S)-Benzoic acid 1-cyclohexyl-hydroxyl-phenyl-2-butynyl ester: Isolated in 41% yield and 99% ee and 80% de as determined by $^{19}$F NMR of the corresponding Mosher ester; colourless oil. $^1$H NMR (300 MHz, CDCl$_3$) δ 8.1-8.0 (m, 2H), 7.6-7.25 (m, 8H), 5.6-5.5 (m, 2H), 2.6-2.5 (m, 1H), 2.0-1.6 (m, 7H), 1.4-1.1 (m, 5H). Anal. Calcd. for $C_{23}H_{24}C_3$: C, 79.28%; H, 6.94%; found: C, 79.01%; H, 6.96%.

(1S,4S)-Benzoic acid 4-tert-butyl-1-cyclohexyl-hydroxy-2-butynyl ester: Isolated in 77% yield and 99% ee and 90% de as determined by HPLC analysis (Chiracel OD, hexane:$^i$PrOH (99:1), 254 nm), t, 15.7 (major), 17.0 (minor), 18.3 (minor); colourless oil. $^1$H NMR (300 MHz, CDCl$_3$) δ 8.1-8.0 (m, 2H), 7.6-7.4 (m, 3H), 5.5 (dd, J=5.9 and 1.5 Hz, 1H), 4.05-4.0 (m, 1H), 2.6-2.5 (m, 1H), 2.1-1.6 (m, 7H), 1.4-1.1 (m, 5H), 1.0 (s, 9H). Anal. Calcd. for $C_{21}H_{28}O_3$: C, Conversion of the chiral dihydroxyalkynes into chiral 1,4 diols may me achieved by hydrogenation using a palladium catalyst. Example 4 describes the hydrogenation of mono- and bis-protected 1,4 dihydroxyalkynes.

Example 4

Hydrogenation of Protected Chiral 1,4 Dihydroxyalkynes (a) Prior to Hydrogenation, a mono-protected 1,4 dihydroxyalkyne may be subjected to a further protection step to protect both chiral hydroxyl groups. For example, to a solution of (1R,4R)-Benzoic acid 4-hydroxy-1,4-dicyclohexyl-2-butynyl ester (177 mg, 0.5 mmol) in CH$_2$Cl$_2$ (5 mL) were added, at 0° C., benzoyl chloride (84 mg, 0.6 mmol), triethylamine (0.08 mL, 0.6 mmol) and DMAP (12 mg, 0.1 mmol). The reaction mixture was stirred at room temperature for 2 h. The mixture was quenched with NH$_4$Cl (aq) and extracted with CH$_2$Cl$_2$ (3×20 mL). The combined organic layers were dried over anhydrous MgSO4 and concentrated in vacuo. The residue was purified by column chromatography on silica gel using pentane:Et$_2$O (15:1). The desired bis-protected alkyne was obtained.

(1R,4R)-Benzoic acid 1,4-dicyclohexyl-2-butynyl diester: Isolated in 92% yield as a colourless oil. $^1$H NMR (300 MHz, CDCl$_3$) δ 8.1-8.0 (m, 4H), 7.6-7.4 (m, 6H), 5.55

(d, J=5.3 Hz, 2H), 2.0-1.6 (m, 12H), 1.4-1.05 (m, 10H). Anal. Calcd. for C$_{30}$H$_{34}$O$_4$: C, 78.57%: H, 7.47%; found: C, 78.60%; H, 7.60%.

(b) Hydrogenation. The mono-protected chiral 1,4 dihydroxyalkyne (550 mg, 1.55 mmol) (194 mg, 0.42 mmol) was dissolved in EtOH (5 mL) under N$_2$ and Pd/C (10% in weight) was added. The nitrogen was evacuated and a balloon with H$_2$ was connected. The mixture was stirred overnight under an atmospheric pressure of H$_2$. The catalyst was filtered off and the EtOH was removed under vacuum. The residue was purified by column chromatography on silica gel using pentane:Et$_2$O (5:1 to 3:1). The desired mono-protected saturated diol was obtained.

(1S,4S)-Benzoic acid 1,4-dicyclohexyl-4-hydroxybutyl ester: Isolated in 45% yield as a white solid, m.p.=106-108° C. Mixture of diastereoisomers (9:1). $^1$H NMR (300 MHz, CDCl$_3$) δ 8.1-8.0 (m, 4H), 7.6-7.4 (m, 6H), 5.1-5.0 (m, 1H), 3.4-3.3 (m, 1H), 2.0-1.4 (m, 12H), 1.35-0.95 (m, 10H). Anal. Calcd. for C$_{23}$H$_{34}$O$_3$: C, 77.05%; H, 9.56%: found: C, 76.91%; H, 9.44%.

Hydrogenation of the bis-protected 1,4 dihydroxyalkyne also yielded the desired protected saturated 1,4 diol.

(1S,4S)-Benzoic acid 1,4-dicyclohexylbutyl diester: Isolated in 71% yield as a white solid, m.p.=123-125° C. Mixture of diastereoisomers (9:1). $^1$H NMR (300 MHz, CDCl$_3$) δ 8.1-8.0 (m, 4H), 7.6-7.4 (m, 6H), 5.1-5.0 (m, 2H), 1.8-1.5 (m, 16H), 1.4-1.0 (m, 10H). Anal. Calcd. for C$_{30}$H$_{38}$O$_4$: C, 77.89%; H, 8.28%; found: C, 77.98%; H, 8.24%.

(c) The chiral 1,4 Diol was obtained by deprotection of the benzoate-protected 1,4 diol as described in example 1, part (b).

(1S,4S)-1,6-dicyclohexyl-1,4-butanediol: Isolated in 87% yield as a white solid, m.p.=153-155° C. Mixture of diastereoisomers (9:1). $^1$H NMR (300 MHz, CDCl$_3$) δ 3.4-3.3 (m, 2H), 2.25 (s broad, 2H), 1.9-1.4 (m, 15H), 1.4-1.0 (m, 12H). Anal. Calcd. for C$_{16}$H$_{30}$O$_2$: C, 75.54%; H, 11.89%; found: C, 75.51%; H, 11.80%.

The reactions described in example 4 are depicted in reaction scheme 4.

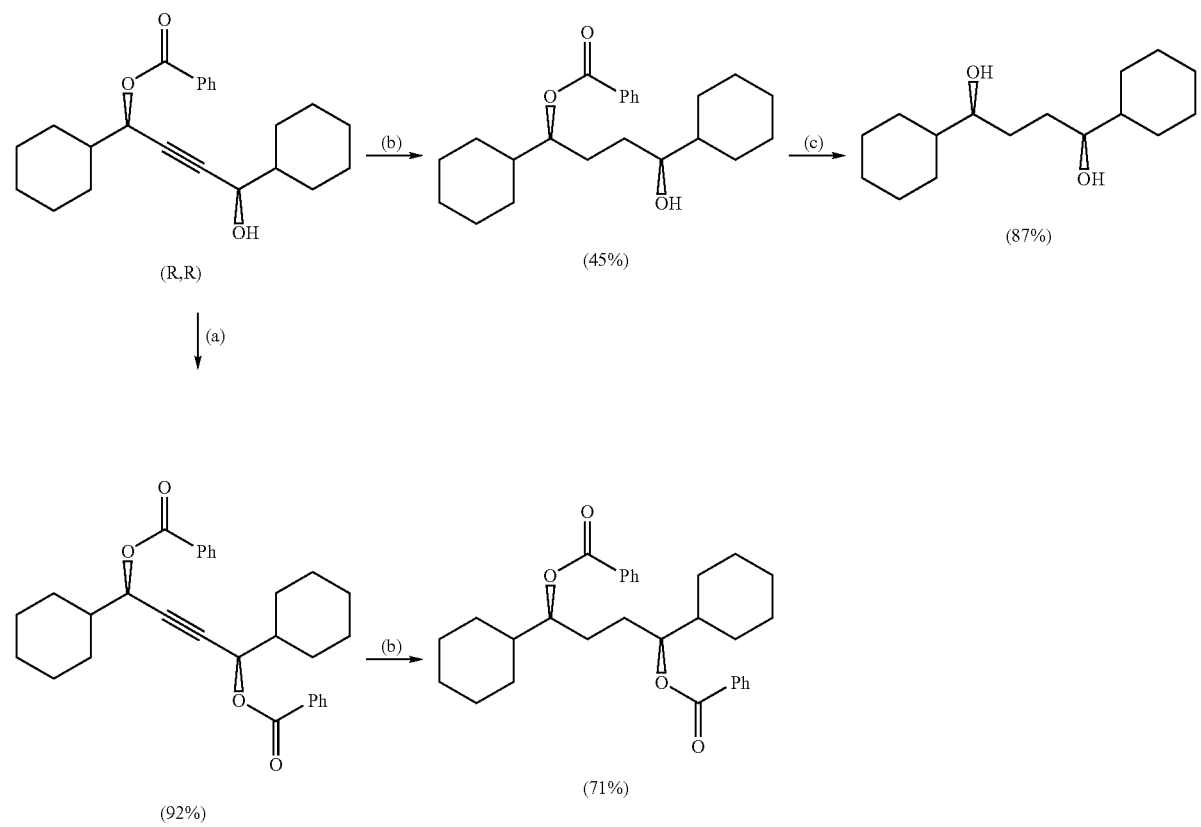

Scheme 4

The invention claimed is:

1. A process for the preparation of a diol comprising the steps of:

(a) Performing an addition reaction between an aldehyde of general formula R$^1$C(O)H in which R$^1$ represents a saturated or unsaturated alkyl (having between 2 and 24 carbon atoms), cycloalkyl or aryl group which may be substituted or unsubstituted and where substituting groups may be alkyl, aryl, halogen, hydroxyl or siloxy groups, and a chiral hydroxyalkyne, in which the hydroxyl group is bound to a chiral centre of general formula R$^2$R$^3$C(OH)(CH$_2$)$_x$C≡CH in which R$^2$ represents a saturated or unsaturated alkyl (having between 2 and 24 carbon atoms), cycloalkyl or aryl group which may be substituted or unsubstituted and where substituting groups may be alkyl, aryl, halogen, hydroxyl or siloxy groups; R$^3$ represents hydrogen or a saturate or unsaturated alkyl (having between 2 and 24 carbon atoms), cycloalkyl or aryl group which may be substituted or unsubstituted and where substituting groups may be alkyl, aryl, halogen, hydroxyl or siloxy groups; $R^2$ and $R^3$ are different and x is 0 to 12, in the presence of a Lewis acid, a chiral ligand capable of reaction with said Lewis acid, and a base, to produce a chiral dihydroxyalkyne and (b) Hydrogenating the chiral dihydroxyalkyne.

2. A process according to claim 1 wherein $R^1$ is selected from the group consisting of ethyl, n-propyl, iso-propyl, n-butyl, iso-butyl, tert-butyl, n-amyl, iso-amyl, tert-amyl, n-hexyl, cyclo-hexyl, phenyl, di-tertbutylphenyl, PhCH=CH and iso-$Pr_3SiO(CH_2)_2$.

3. A process according to claim 1 wherein $R^2$ is selected from the group consisting of ethyl, n-propyl, iso-propyl, n-butyl, iso-butyl, tert-butyl, n-amyl, iso-amyl, tert-amyl, n-hexyl, cyclo-hexyl, phenyl, di-tertbutylphenyl, PhCH=CH and iPr$_3$SiO(CH$_2$)$_2$.

4. A process according to claim 1 wherein x is 0, 1 or 2.

5. A process according to claim 1 wherein the Lewis acid is a metal triflate.

6. A process according to claim 1 wherein step (a) is performed in the presence of the chiral ligand capable of reaction with said Lewis acid and the chiral ligand is a chiral β-diamine or chiral β-thioamine.

7. A process according to claim 6 wherein the chiral ligand is (+) or (−)-N-methylephedrine.

8. A process according to claim 1 wherein the base is a tertiary amine or pyridine.

9. A process according to claim 1 wherein the hydrogenation is performed using a palladium, platinum or nickel catalyst.

10. A process according to claim 1 wherein at least one hydroxyl group in the hydroxyalkyne or dihydroxyalkyne is protected from side reactions during any or all of the steps of the process.

11. A process according to claim 10 wherein the protecting group is a carboxylic acid ester or a sulphonic acid ester.

12. A process for preparing a cyclic phosphine comprising the steps (a) Performing an addition reaction between an aldehyde of general formula $R^1C(O)H$ in which $R^1$ represents a saturated or unsaturated alkyl (having between 2 and 24 carbon atoms), cycloalkyl or aryl group which may be substituted or unsubstituted and where substituting groups may be alkyl, aryl, halogen, hydroxyl or siloxy groups, and a chiral hydroxyalkyne, in which the hydroxyl group is bound to a chiral centre of general formula $R^2R^3C(OH)(CH_2)_xC\equiv CH$ in which $R^2$ represents a saturated or unsaturated alkyl (having between 2 and 24 carbon atoms), cycloalkyl or aryl group which may be substituted or unsubstituted and where substituting groups may be alkyl, aryl, halogen, hydroxyl or siloxy groups; $R^3$ represents hydrogen or a saturated or unsaturated alkyl (having between 2 and 24 carbon atoms), cycloalkyl or aryl group which may be substituted or unsubstituted and where substituting groups may be alkyl, aryl, halogen, hydroxyl or siloxy groups: $R^2$ and $R^3$ are different and x is 0 to 12, in the presence of a Lewis acid, a chiral ligand capable of reaction with said lewis acid, and a base, to produce a chiral dihydroxyalkyne, (b) Hydrogenating the chiral dihydroxyalkyne to produce a chiral dihydroxyalkene, and/or a chiral dihydroxyalkane, and (c) Reacting the dihydroxyalkene and/or dihydroxyalkane with a phosphine species.

13. A process according to claim 3 wherein x is 0, 1 or 2.

* * * * *